United States Patent
Carrel et al.

(10) Patent No.: US 11,413,400 B2
(45) Date of Patent: Aug. 16, 2022

(54) SAFETY ASSEMBLY

(71) Applicant: Becton Dickinson France, Le Pont de Claix (FR)

(72) Inventors: Franck Carrel, Le Pont de Claix (FR); Freddy Mills, Le Pont de Claix (FR)

(73) Assignee: Becton Dickinson France, Le Pont de Claix (FR)

( * ) Notice: Subject to any disclaimer, the term of this patent is extended or adjusted under 35 U.S.C. 154(b) by 392 days.

(21) Appl. No.: 16/647,177

(22) PCT Filed: Sep. 13, 2018

(86) PCT No.: PCT/EP2018/074718
§ 371 (c)(1),
(2) Date: Mar. 13, 2020

(87) PCT Pub. No.: WO2019/053112
PCT Pub. Date: Mar. 21, 2019

(65) Prior Publication Data
US 2021/0030971 A1  Feb. 4, 2021

(30) Foreign Application Priority Data

Sep. 14, 2017 (EP) ..................................... 17306186

(51) Int. Cl.
*A61M 5/32* (2006.01)
*A61M 5/24* (2006.01)
(Continued)

(52) U.S. Cl.
CPC ........ *A61M 5/3202* (2013.01); *A61M 5/2455* (2013.01); *A61M 5/343* (2013.01); *A61M 5/349* (2013.01); *A61B 5/150625* (2013.01); *A61M 2005/2433* (2013.01); *A61M 2005/3217* (2013.01)

(58) Field of Classification Search
CPC .. A61M 5/3202; A61M 5/2455; A61M 5/343; A61M 5/349; A61M 5/3216; A61M 2005/3217; A61B 5/150625
See application file for complete search history.

(56) References Cited

U.S. PATENT DOCUMENTS 7,331,941 B2   2/2008  Vetter et al.
2003/0088215 A1*  5/2003  Ferguson ......... A61B 5/150595
                                                            604/198

FOREIGN PATENT DOCUMENTS

CN           1741829 A      3/2006
CN         203196082 U      9/2013
(Continued)

*Primary Examiner* — Bradley J Osinski
(74) *Attorney, Agent, or Firm* — The Webb Law Firm

(57) ABSTRACT

The invention relates to a safety assembly for preventing needle stick injury with a needle having a proximal end fixed to a tip of a medical container and a pointed distal end, the safety assembly having: an attachment ring fixed to the tip of the container and a safety device to cover at least the distal end of the needle, the safety device attached to the attachment ring. The safety assembly has an attachment ring having an inner ring and an outer ring to be snapped onto each other, the inner ring having an inner recess for applying glue between the inner ring and the tip, and the inner ring and outer ring having mutually engaging elements preventing any rotation of the outer ring relative to the inner ring.

14 Claims, 7 Drawing Sheets

(51) Int. Cl.
 *A61M 5/34* (2006.01)
 *A61B 5/15* (2006.01)

(56) References Cited

FOREIGN PATENT DOCUMENTS

| | | | |
|---|---|---|---|
| EP | 1466638 | A2 | 10/2004 |
| EP | 1535640 | A1 | 6/2005 |
| EP | 1466638 | A3 | 5/2006 |
| WO | 2016/198387 | A1 | 12/2016 |

* cited by examiner

SAFETY ASSEMBLY

CROSS REFERENCE TO RELATED APPLICATIONS

This application is the United States national phase of International Application No. PCT/EP2018/074718 filed Sep. 13, 2018, and claims priority to European Patent Application No. 17306186.2 filed Sep. 14, 2017, the disclosures of which are hereby incorporated by reference in their entirety.

BACKGROUND OF THE INVENTION

Field of the Invention

The present invention relates to a safety assembly for preventing needle stick injury with a needle of a medical device, and also to a medical device provided with such a safety assembly.

Description of Related Art

Medical devices provided with sharp pointed needles are of daily practice among the medical community in order to perform injections into or to take samples from tissues, veins or arteries of the patient. Medical devices having needles may comprise, but not be limited to, injection devices such as syringes, pen-injectors, catheters or blood collection devices. Sharp pointed needles of these medical devices present an inherent risk of needle stick injury to the medical staff and/or the patients and are thus usually covered by a protective cap before use. This cap can preserve the needle not only from contamination but also from undesired contacts or punctures that could occur during transport and delivery of the medical devices. Obviously, such a cap needs to be removed immediately before use of the medical device. Also, similar protection for the needle may also be preferably provided after use of the medical device.

WO 2016/198387 A1 discloses a safety device which comprises a protective cap and a protective arm to be mounted on a tip of a syringe. The safety device is attached to the syringe tip by means of a mounting ring which is to be clipped on a bump formed on the syringe tip.

The protective arm is movable about a pivot axis perpendicular to the axis of the syringe tip between three operative positions:
 a storage position in which the protective arm is interlocked with a protective cap configured to cover at least the distal end of the needle, before use of the syringe,
 a retracted position in which the protective arm releases the protective cap to give access to the needle, in order to allow a user to inject a pharmaceutical composition contained in the syringe into a patient's body, and
 a safety position in which the protective arm covers the needle, after use of the syringe.

During the injection step, the user orients the syringe in a convenient position so that the retracted protective arm does not hinder proper handling of the syringe.

After use, the user has to move the protective arm to the safety position. However, a problem may arise if the protective arm is able to rotate relative to the syringe tip. Indeed, in such case, if the user applies a force to the protective arm that is not exactly along the pivot axis of the protective arm, it may cause the protective arm to rotate about the syringe tip, thus generating a risk of needle stick injury.

Such a rotation of the protective arm relative to the syringe tip may be due to the fact that the syringe is generally sterilized after assembling the mounting ring onto the syringe tip, which may deform the mounting ring and thus reduce the clipping force of the mounting ring.

SUMMARY OF THE INVENTION

In view of the above, an object of the present invention is to improve reliability of the connection between a safety device and a medical container, thereby reducing a risk of the safety device being pulled out and unintentional exposure of a needle of the medical device.

A first aspect of the invention relates to a safety assembly for preventing needle stick injury with a needle having a proximal end fixed to a tip of a medical container and a pointed distal end, said safety assembly comprising:
 an attachment ring configured to be fixed to the tip of the container; and
 a safety device configured to cover at least the distal end of the needle, the safety device being attached to the attachment ring.

Said safety assembly is characterized in that:
 the attachment ring comprises an inner ring and an outer ring configured to be snapped onto each other,
 the inner ring comprises an inner recess configured for applying glue between the inner ring and the tip, and
 the inner ring and outer ring comprise mutually engaging elements preventing any rotation of the outer ring relative to the inner ring.

According to an embodiment, the outer ring comprises an outer peripheral groove and the inner ring comprises at least one inwardly protruding member engaging the peripheral groove of the outer ring.

According to an embodiment, the outer ring comprises at least one inwardly protruding member engaging a proximal end of the inner ring.

The mutually engaging elements may comprise at least one male element and at least one female element complementary to said male element, said male and female elements being configured such that when the outer ring is snapped onto the inner ring, the male element engages the female element.

Advantageously, the male and female elements may have at least two inclined contact surfaces allowing the outer ring to slide relative to the inner ring until the at least one male element engages a respective female element.

According to an embodiment, the inner ring comprises at least two rounded bumps protruding a distal direction and the outer ring comprises a plurality of rounded recesses extending in the distal direction, the rounded recesses being arranged regularly annularly such that the at least two bumps engage two respective recesses when the inner ring and outer ring are snapped onto each other.

According to an alternative embodiment, the inner ring comprises a plurality of recesses extending in a proximal direction and the outer ring comprises at least two fingers extending in the proximal direction, the recesses being arranged regularly annularly such that the at least two fingers engage two respective recesses when the inner ring and outer ring are snapped onto each other.

The inner ring may advantageously comprise at least two axial ribs protruding radially inwardly from the inner surface of the inner ring, the inner recess configured for applying glue being divided in at least two cavities, each extending between a pair of adjacent ribs.

Advantageously, the recess of the inner ring is closed by a proximal circumferential flange extending radially inwardly from the inner surface of the inner ring.

According to an embodiment, said axial ribs are integral with said proximal circumferential flange.

According to a preferred embodiment, the safety device comprises:
- a protective cap configured to cover at least the distal end of the needle; and
- a protective arm attached to the attachment ring, the protective arm being pivotally movable between a storage position in which the protective arm is interlocked with the protective cap, a retracted position in which the protective arm releases the protective cap to give access to the needle, and a safety position in which the protective arm covers the needle.

The outer ring may comprise two inserts protruding radially outwardly for pivotal attachment of the protective arm.

According to an embodiment, the protective arm comprises a proximal leg provided with a cam surface and the protective cap comprises a proximal end provided with an engaging peg, the cam surface and engaging peg being configured such that an axial movement of the protective cap in the distal direction generates a rotary movement of the protective arm relative to the protective cap, thereby displacing the protective arm from the storage position to the retracted position.

Another aspect of the invention relates to a medical device comprising a safety assembly as described above.

Said medical device comprises:
- a medical container having a barrel and a tip extending from the barrel in a distal direction;
- a needle attached to the tip of the medical container; and
- a safety assembly as described above, the inner ring being glued to the tip of the medical container.

The medical container is preferably made of glass.

According to a preferred embodiment, the tip of the medical container is smooth.

BRIEF DESCRIPTION OF THE DRAWINGS

Embodiments of the present invention will be hereinafter described by way of example, with reference to the accompanying figures, in which.

DESCRIPTION OF THE INVENTION

In this application, the distal end of a component or apparatus should be understood as meaning the end farthest from the hand of the user and the proximal end must be understood as meaning the end closest to the hand of the user. As such, the distal direction should be understood as the direction farther away from the hand of the user, and the proximal direction is the opposite direction, i.e., the direction towards the hand of the user. The proximal and distal directions are in parallel to the direction in which a needle of a medical container is to extend. The radial direction should be understood as the direction perpendicular to the proximal and distal directions.

Figure 1:
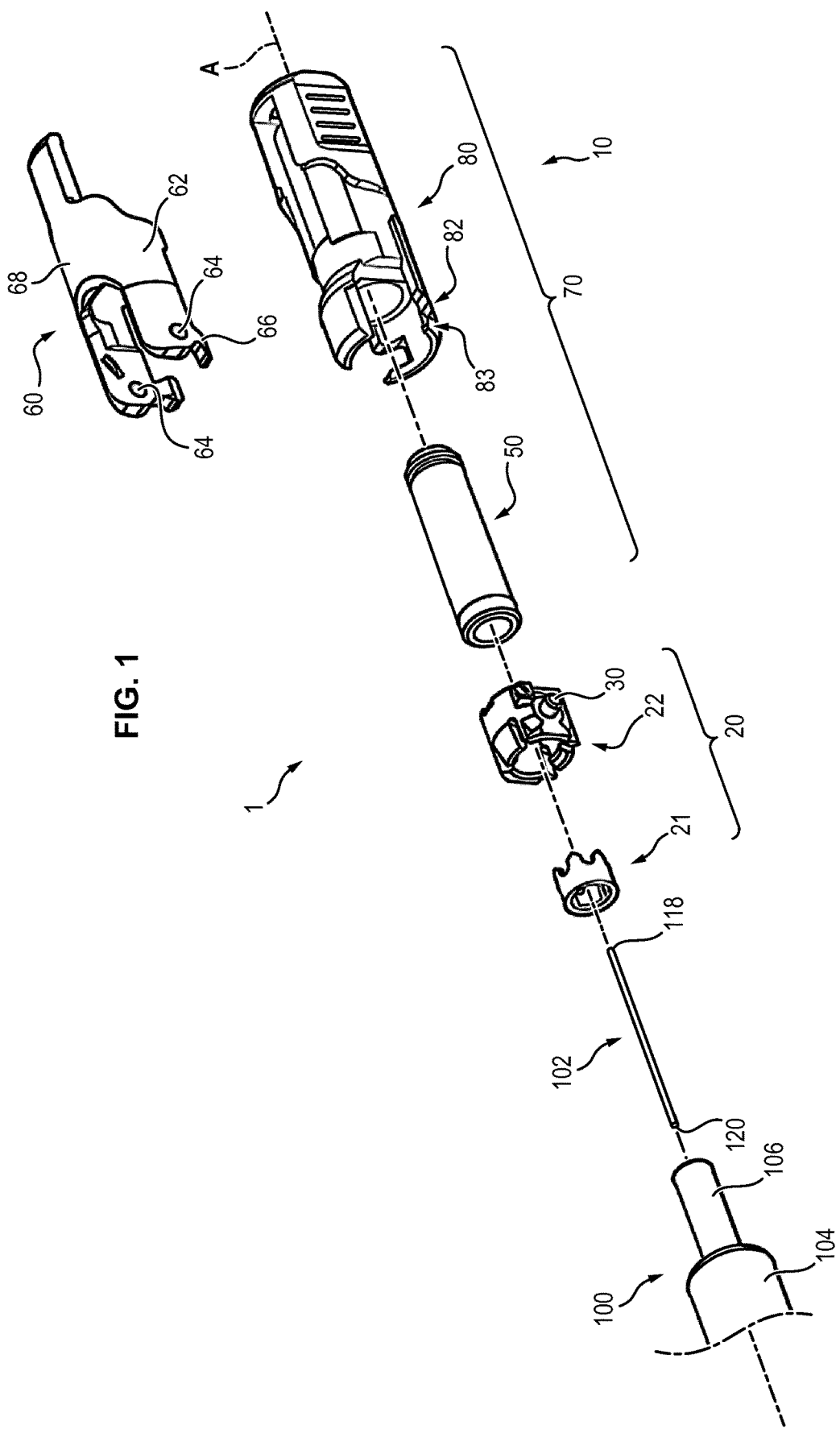
FIG. 1 is an exploded perspective view illustrating a medical device according to an embodiment of the invention.
Figure 2A:
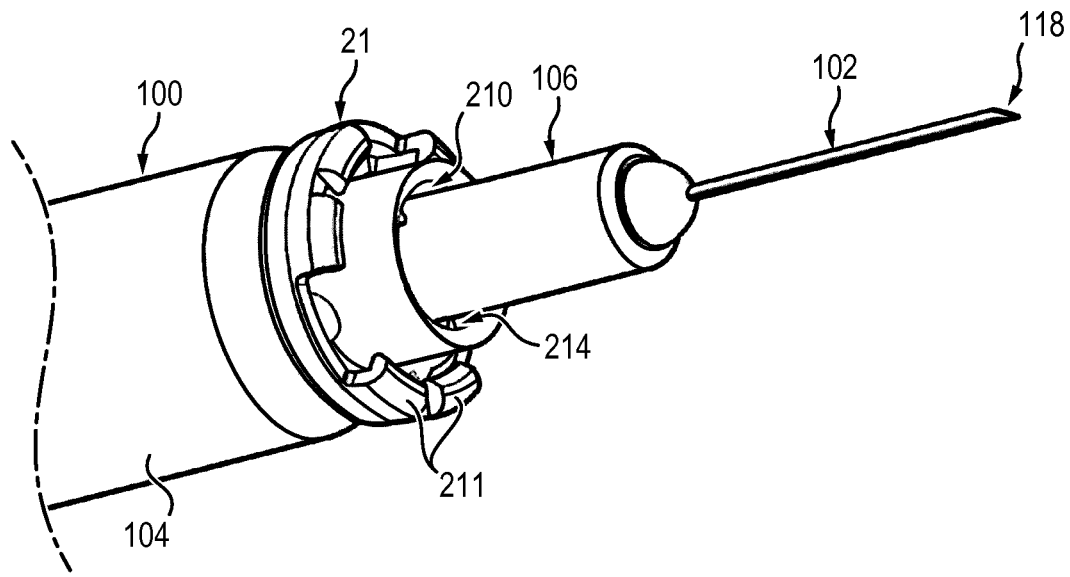
FIGS. 2A and 2B are respectively perspective and cross sectional views of the inner ring mounted on the tip of the medical container, according to a first embodiment.
Figure 2B:
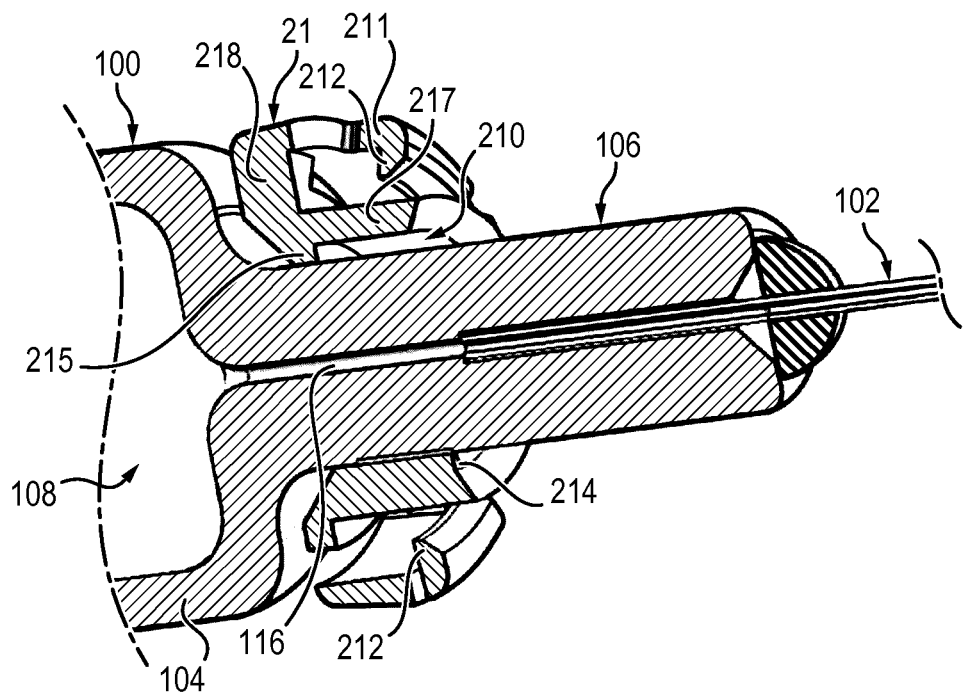

FIG. 1 shows an exploded perspective view illustrating a medical device 1 according to one example. The medical device 1 generally has an elongated shape extending along an axial line A, which may also be referred to as "central axis" in this application.

The medical device 1 comprises a medical container 100 having an elongated barrel 104 and a longitudinal tip 106 extending distally from a distal end of the barrel 104, and a needle 102 attached to the tip 106 of the container 100. The barrel 104 has a tubular shape and defines a reservoir 108 inside thereof for containing a medical solution. At the proximal end of the barrel, the container 100 has a flange (not illustrated) extending radially outwardly. The medical solution which is to be contained in the reservoir 108 may comprise, but not be limited to pharmaceutical composition, vitamins, a vaccine or the like.

The container tip 106 is a generally tubular element having a smaller diameter than the barrel 104. The tip 106 is smoothly connected to the distal end of the barrel 104. The barrel 104 and the tip 106 are preferably made of glass and integrally formed with each other.

The tip 106 defines an inner channel 116 extending through the tip 106 between its proximal and distal ends. The inner channel 116 is in fluid communication with the reservoir 108.

Advantageously, the tip 106 of the container is smooth, i.e. its outer circumferential surface does not comprise any protrusion nor any recess. Thus, the tip has simply a substantially cylindrical or frustoconical shape that is easy to manufacture.

The needle 102 has a pointed distal end 118 and a proximal end 120 which is fixed within the inner channel 116 of the tip 106 by glue or any other known means acceptable to medical use. The needle 102 is a hollow element the inside of which is in fluid communication with the reservoir 108 through the inner channel 116 of the tip 106. When the needle 102 is assembled with the container 100, the distal end 118 of the needle 102 sticks out of the tip 106.

The medical device 1 is provided with a safety assembly 10 for preventing needle stick injury with the needle 102.

The safety assembly 10 comprises an attachment ring 20, and a safety device attached to the attachment ring and intended to cover at least the pointed distal end of the needle.

By "safety device" is meant in the present text a device configured to protect a user from needle stick injury after the injection of the medical solution has been carried out.

According to an embodiment, the safety device comprises a protective arm 60 adapted to be attached to the attachment ring 20, and a protective cap 70 adapted to be inserted on the attachment ring. The protective cap and the protective arm are preferably similar to those described in the patent application WO2016/198387.

The attachment ring 20 comprises an inner ring 21 and an outer ring 22.

The inner ring 21 and the outer ring 22 are preferably made of a plastic suitable to medical use. The inner ring 21 and the outer ring 22 may be made of the same material or of different materials. The material used for the inner ring 21 and the outer ring 22 may comprise, but not be limited to, high density polyethylene (PE), polypropylene (PP), polycarbonate (PC), acrylonitrile butadiene styrene (ABS), polyoxymethylene (POM), polystyrene (PS), polybutylene terephthalate (PBT), polyamide (PA), and their combinations. Using such plastic materials, the inner and outer rings can be provided with suitable shapes (e.g. self-engaging features, sharp edges, etc.) that allow snapping the outer ring to the inner ring with a high pullout resistance.

The inner ring 21 is configured to be glued on the tip of the container. To that end, the inner ring 21 comprises an inner recess 210 configured for applying glue between the inner ring 21 and the tip 106. The inner ring 21 may advantageously comprise at least two, and preferably three, axial ribs 214 extending radially inwardly. The axial ribs 214 are configured to center the inner ring 21 relative to the tip 106 and control the distance between the inner surface of the inner ring and the outer surface of the tip 106, to ensure that a minimal volume is maintained between the inner ring and the tip, thereby allowing distributing a regular amount of glue all over the circumference of the tip. The inner recess for applying glue may thus be divided into several cavities, each extending between two adjacent axial ribs. The inner recess 210 is delimited radially by a longitudinal inner wall 217 of the inner ring, configured to surround the tip 106. Preferably, the inner recess 210 is closed at its proximal end, by a circumferential flange 215 extending radially inwardly from the longitudinal inner wall 217. This flange 215 allows preventing glue from flowing from the proximal end of the inner ring 21. The axial ribs 241 may advantageously be integral with the flange 215.

The glued connection between the inner ring and the tip presents a high pullout resistance.

The outer ring 22 is configured to be snapped onto the inner ring 21. The outer ring is thus retained axially onto the inner ring 21. Both the glued and snapped connections provide to the attachment ring 20 a high pullout resistance with respect to the tip 106. In particular, as compared to a conventional snapped connection between a glass tip comprising a bump protruding radially outwardly and a plastic ring comprising a complementary groove engaging the bump, the snapped connection between the inner and outer rings has a greater pullout resistance. Indeed, glass forming does not allow creating a bump with sharp edges, which is detrimental to the pullout force of the snapped connection. This problem is avoided by providing a smooth glass tip onto which a plastic inner ring can be glued with a sufficient pullout force, and further by creating a strong snapped connection between the inner ring and outer ring that are both made of plastic. As a result, the pullout resistance of the connection between the safety device and the glass tip can be increased.

According to an embodiment (see FIGS. 2A to 5B), the outer ring 22 comprises an outer peripheral groove 221 and the inner ring 21 comprises at least one inwardly protruding member 212 engaging the peripheral groove 221 of the outer ring. For example, said protruding member 212 may extend radially inwardly from an outer peripheral element 211 of the inner ring 21. Preferably, the inner ring comprises a plurality of protruding members 212 distributed over its circumference. To that end, the inner ring 21 comprises a transversal wall 218 that extends radially outwardly from the longitudinal inner wall 217, in the vicinity of the proximal end of the inner wall 217. The outer peripheral element 211 extends distally from the transversal wall 218. The peripheral element 211 has enough flexibility to deflect radially outwardly to allow the proximal end of the outer ring 22 to engage the element 211 until each protruding member 212 engages the peripheral groove 221. For snapping the outer ring 22 onto the inner ring 21, the outer ring 22 is inserted between the inner longitudinal wall 217 and the outer peripheral element 211, until abutting the transversal wall 218, while the protruding member(s) 212 engage the peripheral groove 221. Advantageously, the proximal end of the outer ring 22 may have an outer inclined surface forming a ramp to facilitate its insertion into element 211. Correspondingly, the distal end of each protruding member 212 may have an inner inclined surface configured to cooperate with the proximal end of the outer ring 22 such that said inclined surfaces slide onto each other during assembly of the outer ring onto the inner ring.

According to another embodiment (see FIGS. 6A to 9B), the outer ring 22 comprises at least one inwardly protruding member 220 engaging a proximal end of the inner ring 21. For example, said protruding member 220 may extend radially inwardly from a proximal end of the outer ring. Preferably, the proximal end of the outer ring 22 may comprise a plurality of protruding members 220 distributed over its circumference. In this embodiment, the outer ring 22 covers substantially the whole outer surface of the inner ring 21. The outer ring has enough flexibility to deflect radially outwardly to allow the proximal end of the outer ring 22 to engage the inner ring until each protruding member 212 engages the proximal end of the inner ring 21. Advantageously, the proximal end of the outer ring 22 may have an inner inclined surface forming a ramp to facilitate its insertion onto the inner ring 21. Correspondingly, the distal end of the inner ring 21 may have an inclined outer surface configured to cooperate with the proximal end of the outer ring 22 such that said inclined surfaces slide onto each other during assembly of the outer ring onto the inner ring.

Of course, the above-described embodiments are not intended to be limitative and the invention may apply to any other configuration of snap-in mutual connection of the inner ring and outer ring.

Besides, the inner ring 21 and outer ring 22 comprise mutually engaging elements preventing any rotation of the outer ring 22 relative to the inner ring 21. Said mutually engaging elements may comprise at least one male element and at least one female element complementary to said male element, said male and female elements being configured such that when the outer ring is snapped onto the inner ring, the male element engages the female element.

Figure 5A:
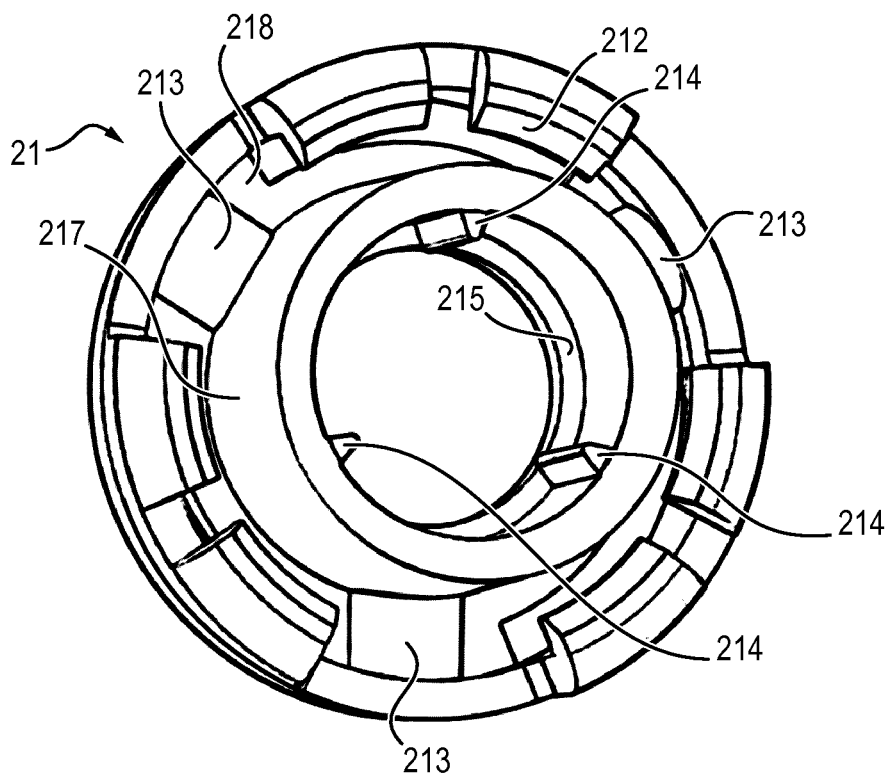
FIGS. 5A and 5B are perspective views of the inner ring and outer ring, respectively, showing mutually engaging elements that prevent any rotation of the outer ring relative to the inner ring, according to the first embodiment.
Figure 5B:
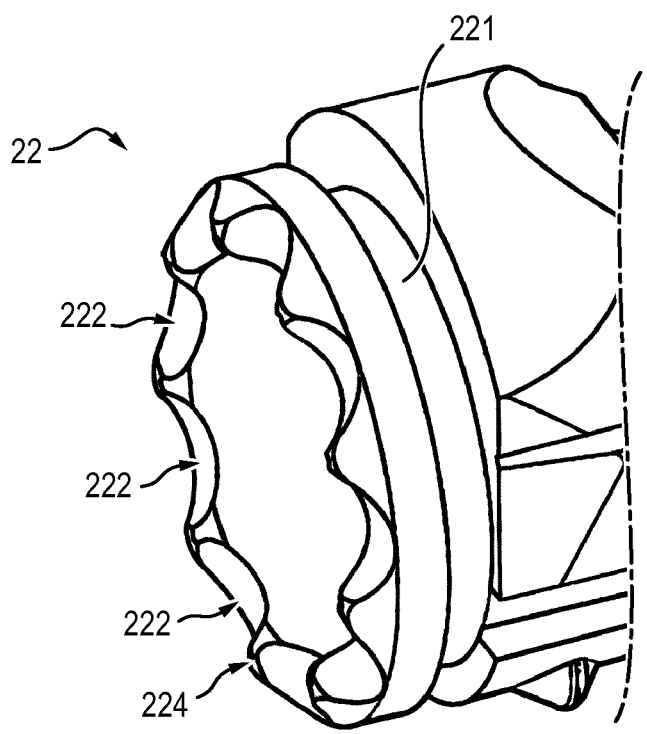
Figure 6A:
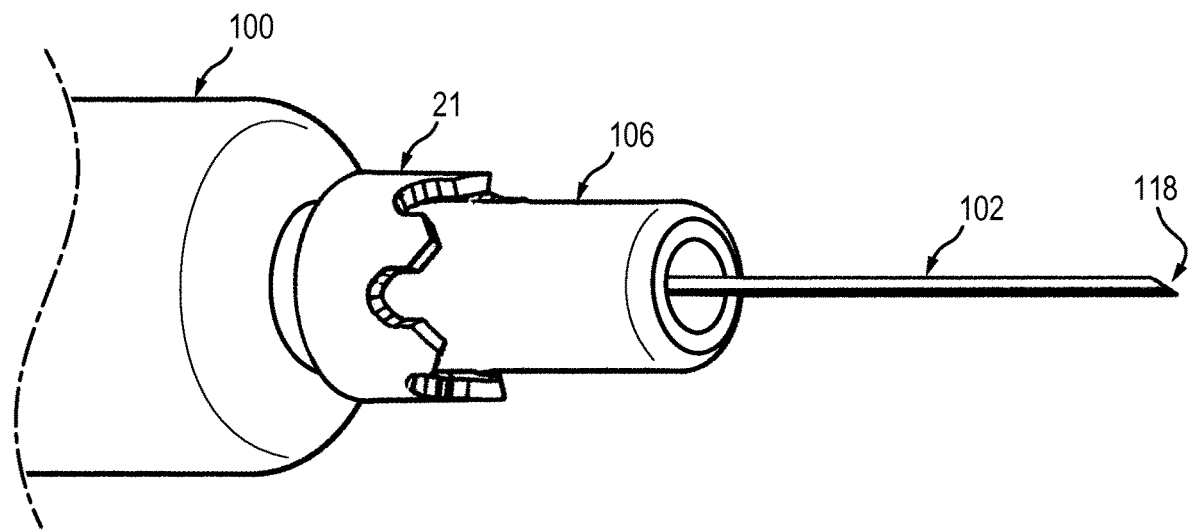
FIGS. 6A and 6B are respectively perspective and cross sectional views of the inner ring mounted on the tip of the medical container, according to a second embodiment.
Figure 6B:
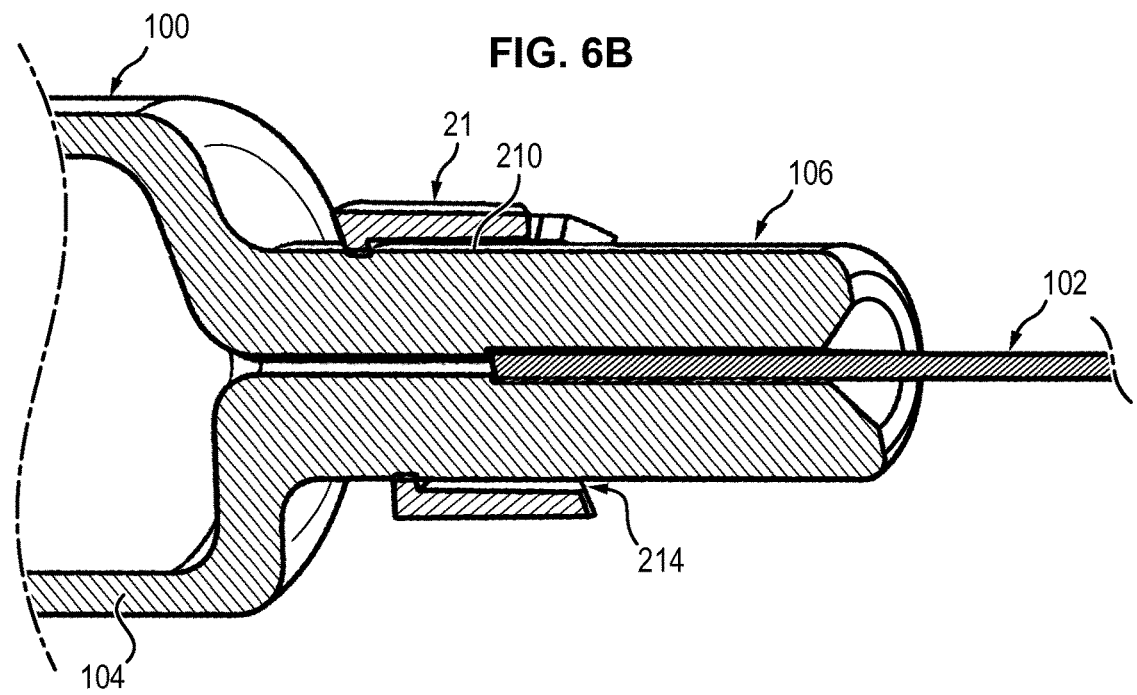

According to an embodiment, represented on FIGS. 5A and 5B, the inner ring 21 comprises at least two rounded bumps 213, and preferably three rounded bumps 213, protruding in a distal direction from the transversal wall 218. The outer ring 22 comprises a transversal wall 224 on the proximal side of the groove 221, with a plurality of rounded recesses 222 formed in the transversal wall 224, in the distal direction. The bumps 213 are arranged at a same distance from the central axis A as the recesses 222. The outer ring comprises at least the same number of recesses 222 as the number of bumps 213. Advantageously, the rounded recesses 222 are arranged regularly annularly such that each bump 213 engages a respective recess 222 when the inner ring and outer ring are snapped onto each other.

Besides, this annular arrangement of the recesses 222, along with the respective inclined contact surfaces of the bumps 213 and recesses 222, provide a self angular orientation of the outer ring relative to the inner ring, without requiring any specific equipment on a machine dedicated to the assembly of the safety device onto the tip of the medical container. Indeed, whatever the relative orientation of the inner and outer rings before their mutual snap-in engagement, even if a recess 222 does not exactly face a respective bump 213 along the central axis, the contact surfaces of the recesses 222 are allowed to slide along the contact surfaces of the bumps 213 under a combined pivotal and axial movement, until each bump 213 fully engages a respective recess 222. In the illustrated embodiment, the inclined contact surfaces of the bumps and recesses are advantageously rounded, which allows a smoother engagement thereof, but they could also comprise straight portions.

It should be noted that the bumps could be located on the outer ring and the recesses on the inner ring without departing from the scope of the invention.

Figure 9A:
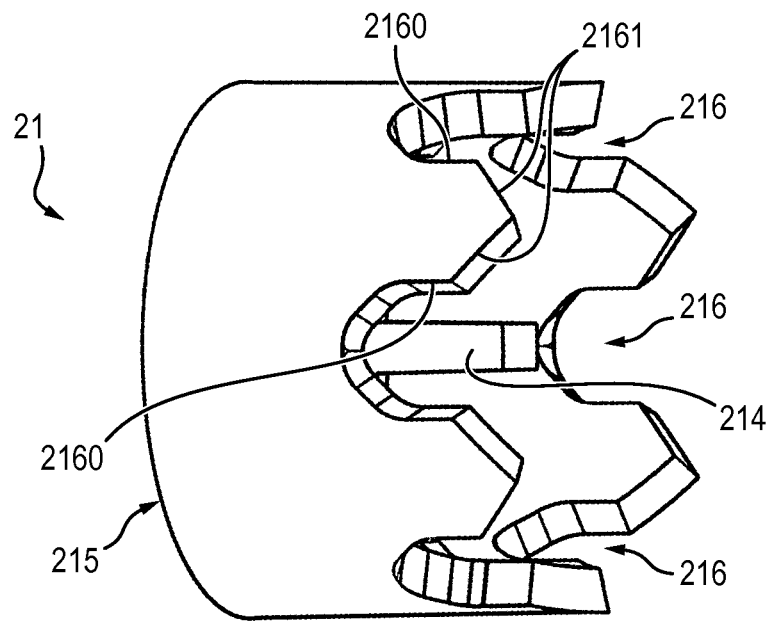
FIGS. 9A and 9B are perspective views of the inner ring and outer ring, respectively, showing mutually engaging elements that prevent any rotation of the outer ring relative to the inner ring, according to the second embodiment.
Figure 9B:
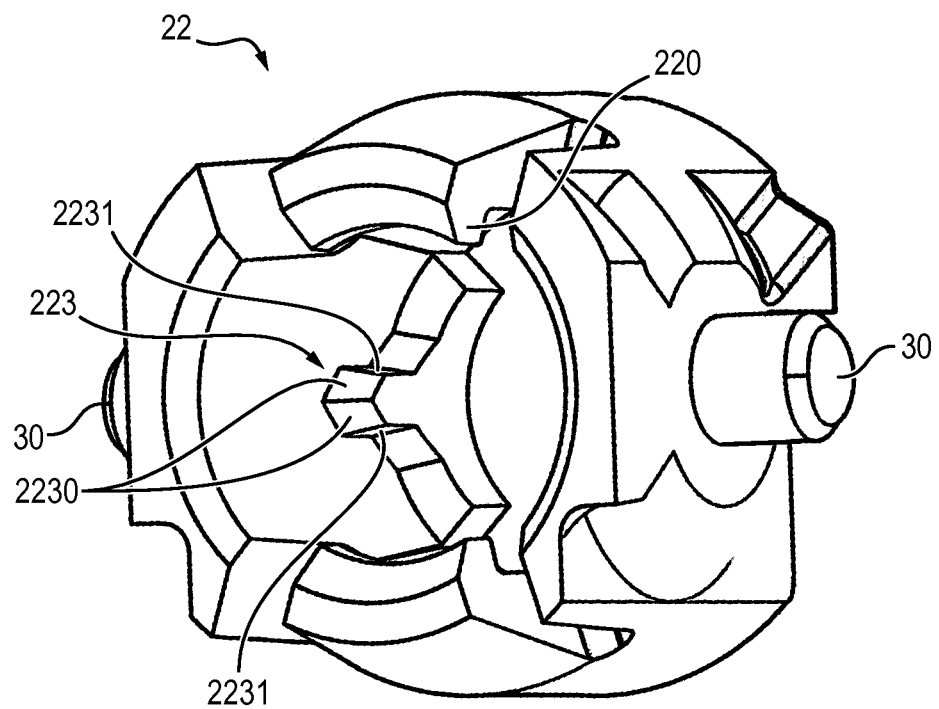

According to another embodiment, represented on FIGS. 9A and 9B, the inner ring 21 comprises a plurality of recesses 216 extending in a proximal direction and the outer ring 22 comprises at least two fingers 223 extending in the proximal direction, along the inner wall of the ring 22. The distal end of the inner ring wherein the recesses 216 are formed has a substantially crenellated shape, wherein adjacent recesses 216 are separated by a tooth defined by two parallel longitudinal walls 2160 extended by two inclined walls 2161 that converge toward each other to form a substantially distal triangular end. The fingers 223 have a pointed proximal end defined by inclined walls 2230 extended distally by parallel longitudinal walls 2231. The fingers 223 are arranged at the same distance from the central axis than the recesses 216. The inner ring comprises at least the same number of recesses 216 as the number of fingers 223. Advantageously, the recesses 216 are arranged regularly annularly such that the at least two fingers 223 engage respective recesses 216 when the inner ring and outer ring are snapped onto each other.

As in the previous embodiment, this annular arrangement of the recesses 216, along with the respective inclined contact surfaces 2230, 2161 of the fingers 223 and recesses 216, provide a self angular orientation of the outer ring relative to the inner ring, without requiring any specific equipment on a machine dedicated to the assembly of the safety device onto the tip of the medical container. Indeed, whatever the relative orientation of the inner and outer rings before their mutual snap-in engagement, even if a recess 216 does not exactly face a respective finger 223, the contact surfaces 2230 of the fingers 223 may be allowed to slide along the contact surfaces 2161 of the recesses 216 under a combined pivotal and axial movement, until each finger 223 fully engages a respective recess 216.

It should be noted that the fingers could be located on the inner ring and the recesses on the outer ring without departing from the scope of the invention. Besides, the shape of the fingers and recesses of the latter embodiment could be used with the snapped connection of the inner and outer rings of the previous embodiment without departing from the scope of the invention.

The safety device—e.g. comprising the protective arm 60 and the protective cap 70 in the embodiment illustrated in FIGS. 1, 3, 4, 7 and 8—is adapted to be mounted on the tip of the medical container by means of the attachment ring to cover the needle.

In the embodiment illustrated in FIG. 1, the protective cap 70 comprises a needle shield 50 and a rigid shield 80. The needle shield 50 is a tubular element defining an inner cavity for accommodating the needle 102. The needle shield 50 is advantageously made of an elastomeric material and dimensioned to be accommodated by the rigid shield 80. The protective arm 60 and the rigid shield 80 may be made of plastic.

It is to be noted that the protective cap 70 is illustrated by way of example and may also have other configurations, as long as it provides protection against needle stick injury with the needle 102 before use. For example, the protective cap 70 may comprise only one shield, e.g. the rigid shield 80.

Besides, the invention is not limited to a safety device comprising a protective cap and a protective arm as illustrated in FIGS. 1, 3, 4, 7 and 8, but to any safety device intended to be attached to the tip of the medical container. To that end, the safety device comprises a part configured to be attached to the outer ring 22. For sake of concision only and without any intended limitation, the following description is based on the safety device illustrated in FIGS. 1, 3, 4, 7 and 8.

Returning to FIG. 1, the protective arm 60 is attached to the outer ring 22 by a pivot link such that it may adopt:
- a storage position where it is interlocked with the protective cap 70;
- a retracted position where it gives access to the needle 102; and
- a safety position where it covers the needle 102.

To that end, the outer ring 22 comprises fixing means configured to pivotally attach the protective arm to the outer ring 22. The fixing means may for example comprise inserts 30 (only one of them is visible in FIG. 1) sticking out radially outwardly from the outer ring, while the protective arm 60 comprises openings 64 configured to receive the inserts 30 so as to allow rotation of the protective arm with respect to the outer ring.

The protective cap 70 comprises a proximal extremity provided with at least one engaging peg 83 defining a recess 82.

The protective arm 60 has a distal cover 68 and two legs 62 extending from the distal cover 68 in the proximal direction. Although not illustrated in the drawings, the distal cover 68 may comprise a notch intended to accommodate the distal end 118 of the needle 102.

The protective arm 60 comprises a cam surface 66 at the proximal extremity of at least one leg 62, said cam surface being configured to be accommodated in the recess 82. The cam surface 66 of the protective arm and the engaging peg 83 of the protective cap cooperate so that an axial movement of the protective cap 70 in the distal direction generates a rotary movement of the protective arm 60 relative to the outer ring 22.

In the storage position, the protective arm 60 is interlocked with the protective cap 70, which covers the distal end 118 of the needle 102. In this position, the protective arm 60 cooperates with the protective cap 70 to prohibit access to the needle 102, thereby preventing needle stick injury during transportation, delivery or storage of the medical device 1.

When the protective cap 70 as well as the needle shield 50 is moved in the distal direction, the engaging peg 83 pushes the cam surface 66 of the protective arm 60, resulting in a rotary movement of the protective arm 60 with respect to the outer ring 22, to the retracted position.

In the retracted position, the protective arm 60 is substantially at right angle relative to the needle 102, and the rigid shield 80 is completely removed from the protective arm 60. At that time, the safety assembly 10 is open to give full access to the needle 102. The medical device 1 is ready to use, for example to inject a medical product into the body of a patient.

Once the injection is performed, the user may apply a force to the protective arm 60 to rotate the protective arm 60 back in order to cover the needle 102 with the protective arm 60. The protective arm is thus in the safety position.

The safety assembly is assembled as follows. At an industrial scale, the assembling process is advantageously carried out by a machine, wherein the medical container is held and the components of the safety assembly are assembled to the tip.

Figure 3:
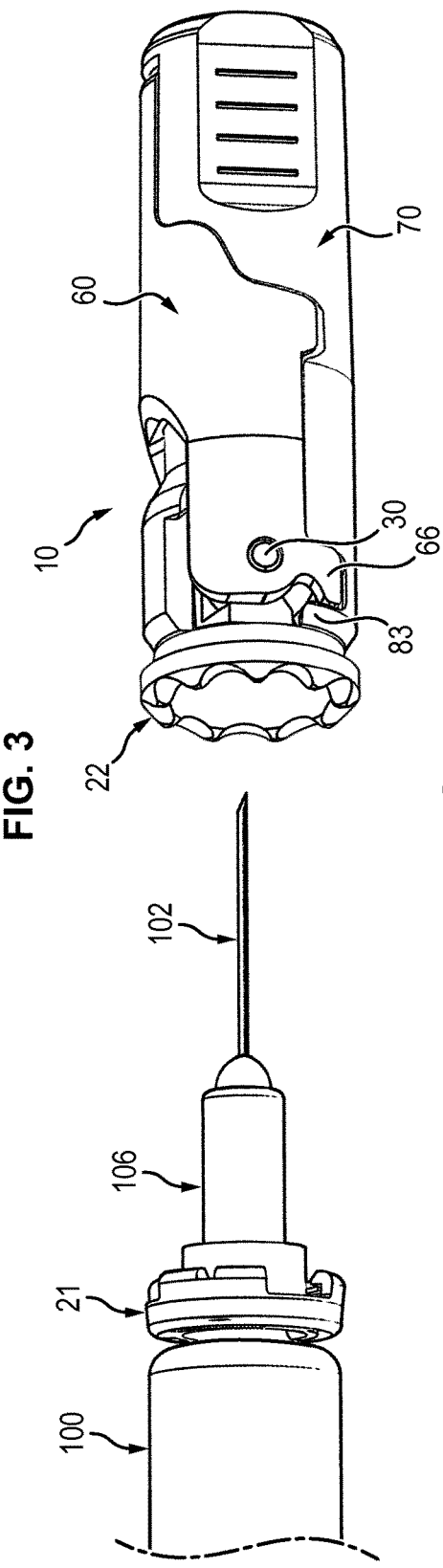
FIG. 3 is a perspective view illustrating a step of assembling the safety assembly onto the inner ring, according to the first embodiment.
Figure 4:
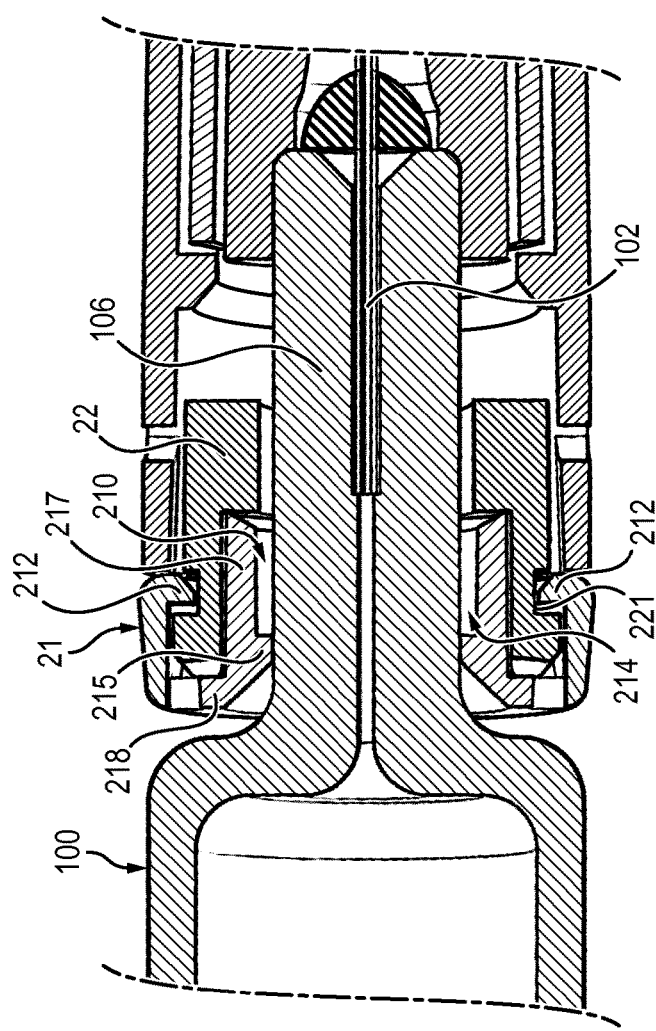
FIG. 4 is a cross sectional view showing the safety assembly mounted on the inner ring, according to the first embodiment.
Figure 7:
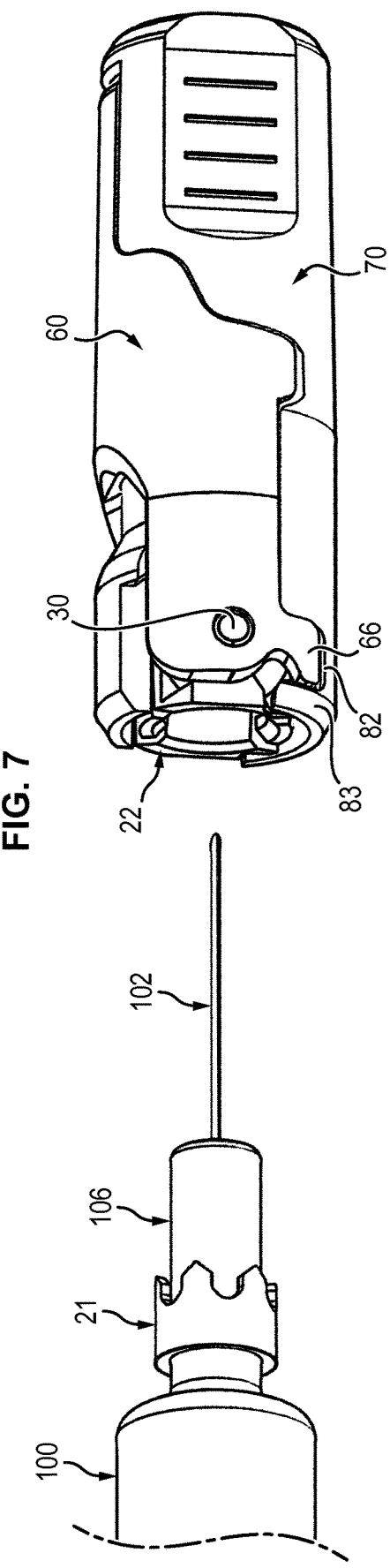
FIG. 7 is a perspective view illustrating a step of assembling the safety assembly onto the inner ring, according to the second embodiment.
Figure 8:
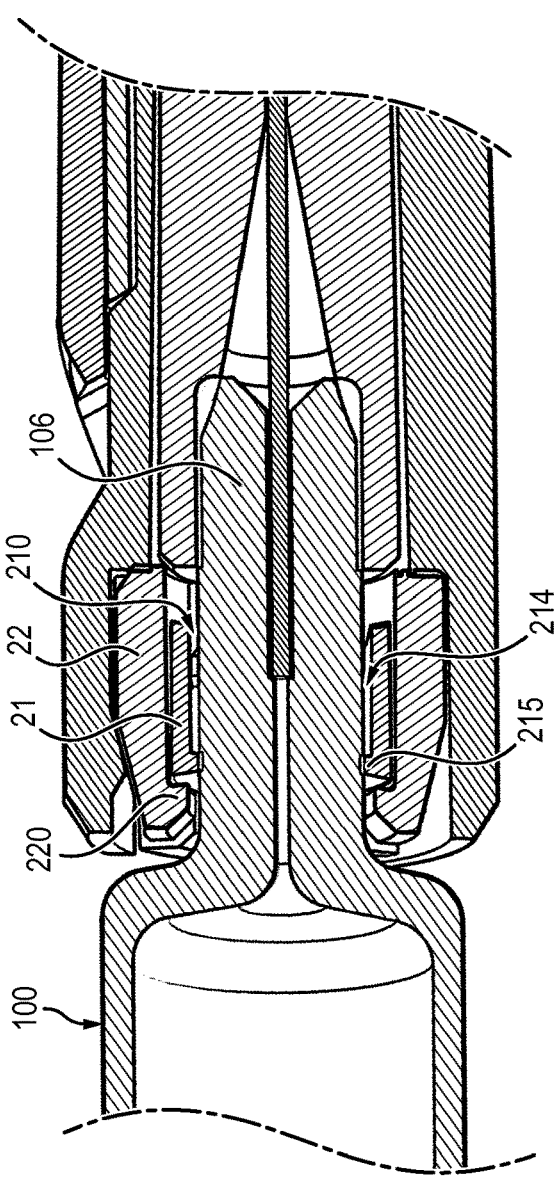
FIG. 8 is a cross sectional view showing the safety assembly mounted on the inner ring, according to the second embodiment.

First, as shown in FIG. 3 or FIG. 7, the inner ring 21 is glued to the tip of the medical container 106. The outer ring 22, protective cap 60 and protective arm 70 are assembled together and inserted as a whole onto the tip 106.

As explained above, the outer ring 22 orients relative to the inner ring 21 by sliding the contact surfaces of the engaging elements of the outer ring (e.g. recesses 222 or fingers 223 in the above-described embodiments) along the contact surfaces of the engaging elements of the inner ring (e.g. bumps 213 or recesses 216 in the above-described embodiments), until a full engagement of the respective elements. At the same time, the snap-in connection of the inner and outer ring is completed (see FIG. 4 or 8). Thus, the outer ring is prevented from any axial or rotational movement relative to the inner ring.

The safety assembly is then operable.

REFERENCES

WO 2016/198387 A1

The invention claimed is:

1. A safety assembly for preventing needle stick injury with a needle, the needle having a proximal end fixed to a tip of a medical container and a pointed distal end, the safety assembly comprising:
   an attachment ring configured to be fixed to the tip of the medical container;
   a safety device configured to cover at least the distal end of the needle, the safety device being attached to the attachment ring;
   wherein:
   the attachment ring comprises an inner ring and an outer ring configured to be snapped onto each other,
   the inner ring comprises an inner recess configured for applying glue between the inner ring and the tip of the container,
   the inner ring and outer ring comprise mutually engaging elements preventing any rotation of the outer ring relative to the inner ring,
   the mutually engaging elements comprise an at least one male element and an at least one female element complementary to said male element, said male and female elements being configured such that when the outer ring is snapped onto the inner ring, the male element engages the female element, and
   the male and female elements have at least two inclined contact surfaces allowing the outer ring to slide relative to the inner ring under a combined pivotal and axial movement until the at least one male element engages a respective female element.

2. The safety assembly of claim 1, wherein the outer ring comprises an outer peripheral groove and the inner ring comprises an at least one inwardly protruding member engaging the peripheral groove of the outer ring.

3. The safety assembly of claim 1, wherein the outer ring comprises an at least one inwardly protruding member engaging a proximal end of the inner ring.

4. The safety assembly of claim 1, wherein the inner ring comprises at least two rounded bumps protruding in a distal direction and the outer ring comprises a plurality of rounded recesses extending in the distal direction, the rounded recesses being arranged regularly annularly such that the at least two bumps engage two respective recesses when the inner ring and outer ring are snapped onto each other.

5. The safety assembly of claim 1, wherein the inner ring comprises a plurality of recesses extending in a proximal direction and the outer ring comprises at least two fingers extending in the proximal direction, the recesses being arranged regularly annularly such that the at least two fingers engage two respective recesses when the inner ring and outer ring are snapped onto each other.

6. The safety assembly of claim 1, wherein the inner ring comprises at least two axial ribs protruding radially inwardly from an inner surface of the inner ring, the inner recess configured for applying glue being divided in at least two cavities, each extending between a pair of adjacent ribs.

7. The safety assembly of claim 6, wherein the inner recess of the inner ring is closed by a proximal circumferential flange extending radially inwardly from an inner surface of the inner ring and the axial ribs are integral with the proximal circumferential flange.

8. The safety assembly of claim 1, wherein the inner recess of the inner ring is closed by a proximal circumferential flange extending radially inwardly from an inner surface of the inner ring.

9. The safety assembly of claim 1, wherein the safety device further comprises:
   a protective cap configured to cover at least the distal end of the needle; and
   a protective arm attached to the attachment ring, the protective arm being pivotally movable between a storage position in which the protective arm is interlocked with the protective cap, a retracted position in which the protective arm releases the protective cap to give access to the needle, and a safety position in which the protective arm covers the needle.

10. The safety assembly of claim 9, wherein the outer ring comprises two inserts protruding radially outwardly for pivotal attachment of the protective arm.

11. The safety assembly of claim 10, wherein the protective arm comprises a proximal leg provided with a cam surface and the protective cap comprises a proximal end provided with an engaging peg, the cam surface and engaging peg configured such that movement of the protective cap in the distal direction generates a rotary movement of the protective arm relative to the protective cap, thereby displacing the protective arm from the storage position to the retracted position.

12. A medical device comprising:
a medical container having a barrel and a tip extending from the barrel in a distal direction;
a needle attached to the tip of the medical container; and
a safety assembly according to claim 1, the inner ring being glued to the tip of the medical container.

13. The medical device of claim 12, wherein the medical container is made of glass.

14. The medical device of claim 12, wherein the tip of the medical container is smooth.

* * * * *